United States Patent
Newton et al.

(10) Patent No.: US 7,032,594 B2
(45) Date of Patent: Apr. 25, 2006

(54) DEVICE FOR ADMINISTERING DOSES OF PARTICULATE MATERIAL

(75) Inventors: Michael Edgar Newton, Norfolk (GB); Simon James Smith, Hertford (GB); Dominic Charles Reber, Veyey (CH); Roger William Clarke, Histon (GB); Peter Alan Evans, Cambs (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/381,691

(22) PCT Filed: Sep. 26, 2001

(86) PCT No.: PCT/GB01/04296

§ 371 (c)(1),
(2), (4) Date: Sep. 22, 2003

(87) PCT Pub. No.: WO02/26302

PCT Pub. Date: Apr. 4, 2002

(65) Prior Publication Data

US 2004/0060557 A1    Apr. 1, 2004

(30) Foreign Application Priority Data

Sep. 27, 2000   (GB) .................................... 0023654

(51) Int. Cl.
*A61M 15/00*    (2006.01)
(52) U.S. Cl. ............................. 128/203.15; 128/203.19
(58) Field of Classification Search ........... 128/200.22, 128/200.23, 203.12, 203.15, 203.21, 203.24, 128/200.17, 200.21, 203.19
See application file for complete search history.

(56) References Cited

U.S. PATENT DOCUMENTS

| 5,301,666 A | | 4/1994 | Lerk | |
| 5,533,502 A | * | 7/1996 | Piper | 128/203.21 |
| 5,740,794 A | * | 4/1998 | Smith et al. | 128/203.15 |
| 6,732,732 B1 | * | 5/2004 | Edwards et al. | 128/203.21 |
| 6,792,945 B1 | * | 9/2004 | Davies et al. | 128/203.15 |

FOREIGN PATENT DOCUMENTS

| EP | 0211595 A2 | | 2/1987 |
| WO | WO 95/31238 | * | 11/1995 |
| WO | WO-95/31238 A1 | | 11/1995 |

* cited by examiner

*Primary Examiner*—Teena Mitchell
(74) *Attorney, Agent, or Firm*—Barnes & ThornburgLLP

(57) ABSTRACT

An inhaler for dispensing medicament in the form of a dry powder is powder is provided with an airway (50) through which a dose travels from an ejection zone to an outlet of the airway. The airway (50) has an inlet means which is so arranged as to create a jacket of air, flowing through a part of the airway extending from the ejection zone to the outlet. The jacket of air surrounds said dose and thereby prevents it form impinging on the airway walls. This reduces accumulation of material on the airway walls, and thus improves the consistency of performance of the inhaler. Preferably, the inlet means includes a throat for producing a stream of fast flowing air which creates a zone of low pressure in front of the ejection zone, thereby to facilitate ejection of a dose.

10 Claims, 18 Drawing Sheets

DEVICE FOR ADMINISTERING DOSES OF PARTICULATE MATERIAL

FIELD OF THE INVENTION

This invention relates to devices for administering doses of particulate material, in particular to inhalers for dispensing single doses of powdered medicament.

BACKGROUND OF THE INVENTION

The self administration by inhalation of a pharmacologically active compound is becoming increasingly common in the treatment of various conditions, particularly respiratory problems such as asthma. Such a compound can be provided in a finely divided particulate form in a dispenser, commonly referred to as an inhaler.

The user of such a device self administers a dose of the compound by inhaling through a mouthpiece. This sets up a flow of air which ejects the dose of particulate material from the device. An example of such a device is shown in European Patent specification No. EP 0211595 (Glaxo Group Limited), and has a disc-shaped blister pack for containing a number of individually encapsulated doses of dry powder medicament, and a powder dilutant such as lactose. Numerous other designs of inhaler have been proposed, for example, the inhaler shown in U.S. Pat. No. 5,301,666, in which the doses of particulate material are contained in compartments in a series of rings that are rotated and moved axially to bring each compartment in turn into registry with an airway in the device.

The volume and flow rate of air inhaled through an inhaler may vary considerably from one use to another, particularly if the user has a respiratory complaint, the symptoms of which may vary in their severity.

The variation in rate of flow and/or volume of air inhaled can cause variations in the amounts of powder ejected from the device. The effect that this variation has on the amount of pharmacologically active compound which is actually administered each time the device is used is small if the device stores the compound mixed together with a relatively large amount of dilutant. However, it is desirable for the compound to be stored with relatively little or no dilutant, as more doses of material can be stored in an inhaler of a given size if the compound is relatively concentrated. In addition, the administering of a dose of medicament with little or no dilutant requires the user to inhale a smaller volume of powder, which is less likely to leave an unpleasant sensation in the user's mouth and throat.

However, in such cases, the variations in the amount of powder ejected from the inhaler can cause significant variations in the amount of dose actually administered to the user.

SUMMARY OF THE INVENTION

According to a first aspect of the invention, there is provided a device for dispensing doses of particulate material, the device comprising an airway having an inlet means through which air is drawn into the airway, and an outlet through which doses of particulate material are dispensed, the device further comprising receiving means for receiving and retaining a dose of material in an ejection zone in registry with the airway, from which ejection zone, in use, a dose travels to the outlet, wherein the inlet means includes at least one inlet so positioned as to direct a flow of air into the region between a dose exiting the ejection zone and the wall of the airway, thereby providing, in use, a jacket of air, flowing from the ejection zone to the exit, which prevents particles of the ejected dose from impinging on the airway walls.

It has been found that the deposition of particulate material on the walls of an airway of an inhaler significantly affects the amount of material actually administered each time the inhaler is used. The jacket of air produced by the device according to the present invention at least reduces the amount of material deposited on the airway walls, and therefore improves the consistency of the performance of the device.

In order to create said jacket of air, the inlet means preferably surrounds the ejection zone, and hence any dose therein. Preferably, therefore, the inlet means comprises an annular inlet.

The inlet means may to advantage comprise a further inlet situated behind the ejection zone so that said zone is interposed between the further inlet and the outlet, so that the pressure of air passing through the further inlet ejects the dose from the ejection zone.

Thus, the inlet means, in effect, creates two streams of air, one in which the dose is entrained, and another which defines the jacket.

Preferably, the inlet means is so configured as to accelerate the flow of air which is to define said jacket as that air enters the passageway thereby to create a zone of low pressure in front of the ejection zone. Thus, the dose is drawn out of the cavity by the fast flowing air that is to form the jacket. It has been found that, in general, the fast flowing air will create a zone of lower pressure in front of the dose than would be the case if the sole source of low pressure were the suction applied by the user, and this feature therefore facilitates the ejection of the dose, particularly for a user whose breathing is impaired.

In that connection, the inlet means preferably includes a throat for accelerating the flow of air which is to define said jacket as that air enters the passageway. Thus, the throat acts as a venturi for drawing the dose out of the ejection zone.

Preferably, the receiving means is so arranged as to receive a container having a plurality of compartments, each containing a respective dose, and the device includes indexing means for moving the container so as to bring successive compartments into the ejection zone.

Preferably, the device constitutes an inhaler for dispensing doses of a powdered medicament by inhalation, the outlet of the airway forming part of the mouthpiece of the inhaler.

Preferably, the receiving means comprises an elongate cylindrical cavity for receiving a cylindrical container having a plurality of radial apertures, each constituting a respective compartment, the device having indexing means for rotating the container about and moving the container along its axis so as to bring successive apertures into said ejection zone.

A cylindrical container provides a relatively compact means of holding a number of doses. Furthermore, the improved dispensing consistency provided by an inhaler according to the invention enables the particulate material to be contained in the cylinder with relatively little or no dilutant, thus enabling the cylinder to be designed to contain a large number of doses.

Preferably, the portion of the airway extending from the ejection zone to the mouthpiece is substantially radial relative to the cylindrical cavity. This enables that portion of the airway to be relatively short, and thus further reduces the chances of material being deposited on the airway walls.

Preferably, the device is arranged for use with a container having pierceable sealing means for individually encapsulating the doses, the device including a piercing mechanism for piercing receiving means to allow each dose, in turn, to be dispensed, wherein the piercing mechanism and indexing means are operatively linked to a control member movable in one direction to operate the indexing means and in the other to operate the piercing mechanism, the device including a non-return mechanism for preventing movement of the control member in one of the directions until the previous stroke of the movement in the other direction has been completed.

Thus, the non-return mechanism ensures that the indexing means has been properly operated, so that a fresh dose is properly in registry with the piercing member before the latter is operated.

Preferably, the control member is rotatable, and the non-return means comprises a two-way ratchet mechanism operable to ensure that, for both senses of rotational movement of the member, a full stroke of movement in either sense is completed before the next stroke of movement in the opposite sense commences.

Conveniently, the non-return mechanism may comprise a pair of oppositely directed pawls on a carrier mounted on a control member or a body of the device, and operable to engage teeth fixed relative to the other of the control member and the body of the device, the mechanism further comprising abutment means for engaging the carrier at the end of each stroke to move one pawl out of engagement with the teeth and bring the other pawl into said engagement.

BRIEF DESCRIPTION OF THE DRAWINGS

The invention will now be described, by way of example only, with reference to the accompanying drawings, in which.

DETAILED DESCRIPTION

Figure 1:
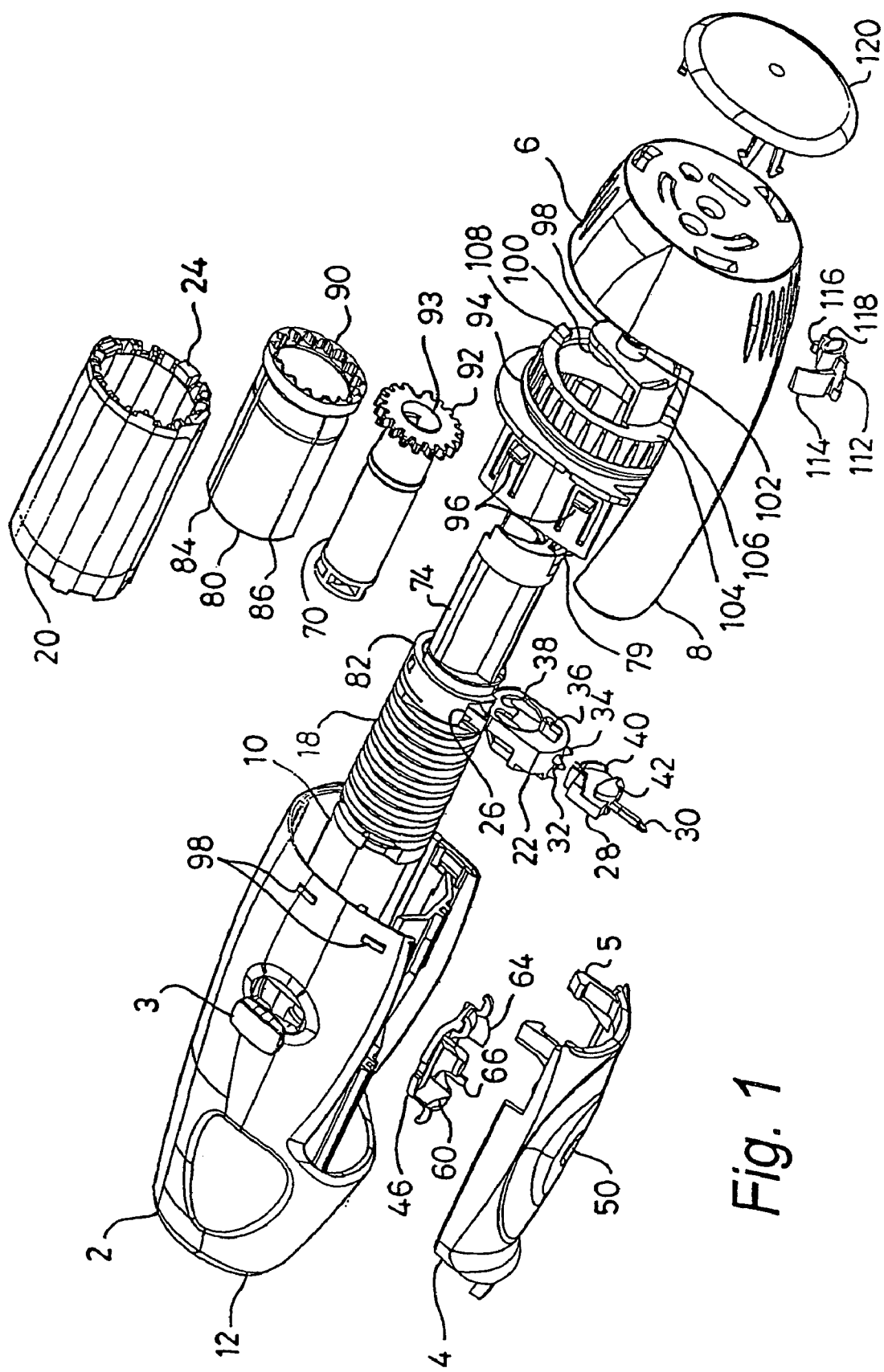
FIG. 1 is an exploded isometric view of an inhaler in accordance with the invention.
Figure 2:
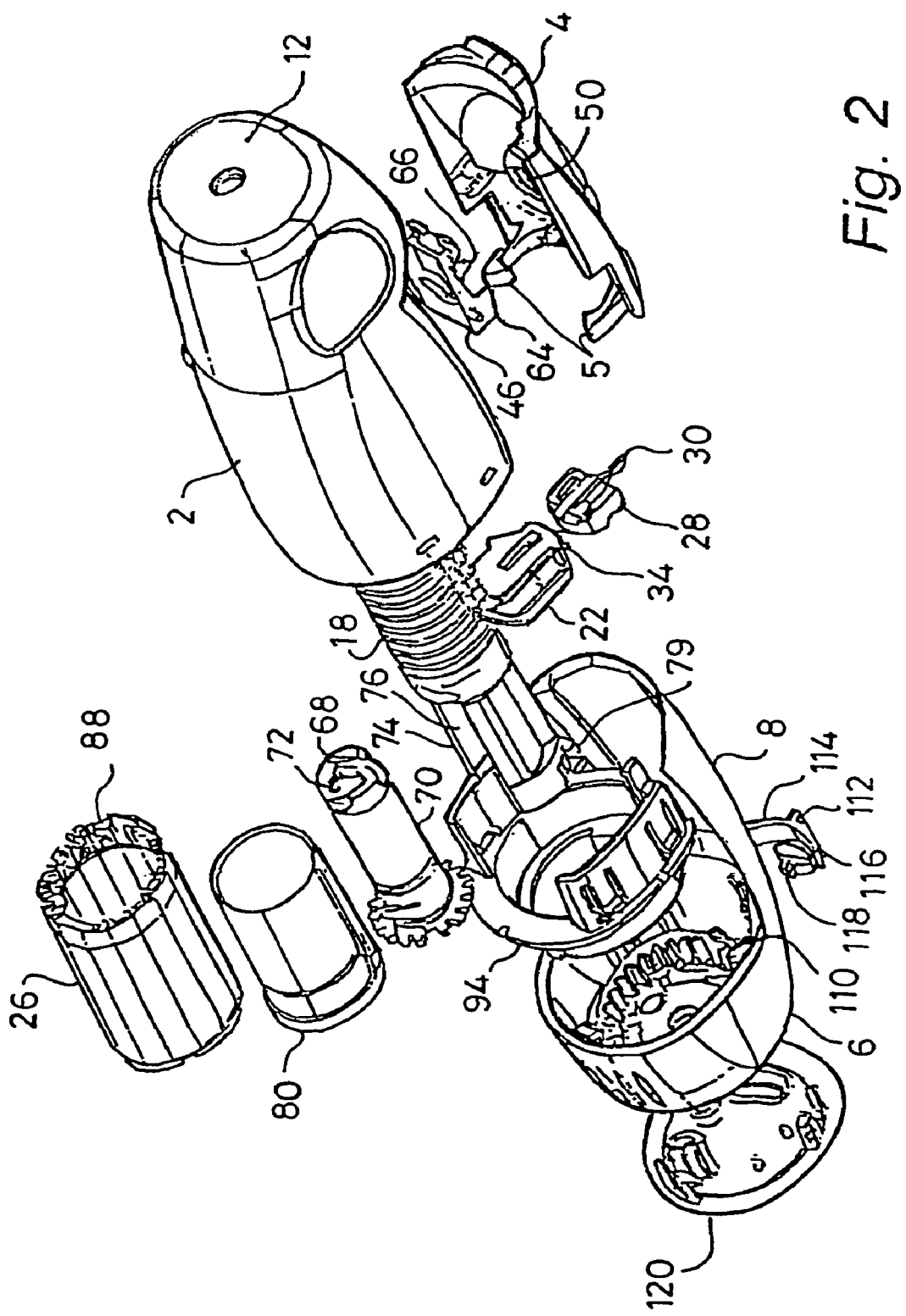
FIG. 2 is a similarly exploded view of the inhaler when rotated through 180° relative to FIG. 1.

With reference to FIGS. 1 and 2, an inhaler comprises an elongate shell 2, at one side of which a mouthpiece 4 is attached. The inhaler includes a rotatable control member 6 which is situated at one end of the shell 2 and which incorporates a cover 8 for covering the mouthpiece 4 when the inhaler is not in use. The shell 2 is fitted with a window 3, through which a container (of medicament) in the inhaler can be viewed.

Figure 15:
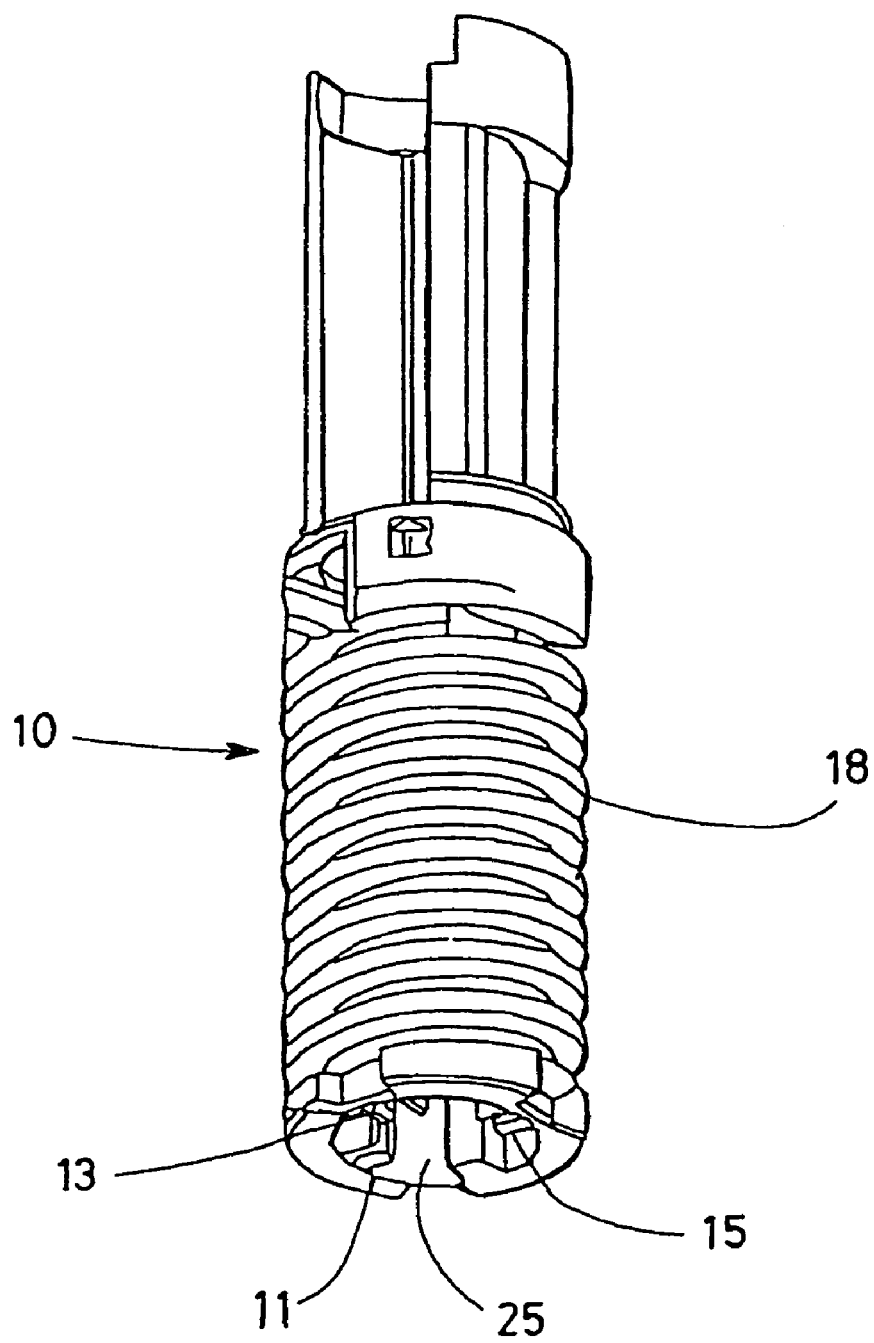
FIG. 15 is a perspective view, from a different angle, of one of the components shown in FIG. 4.
Figure 16:
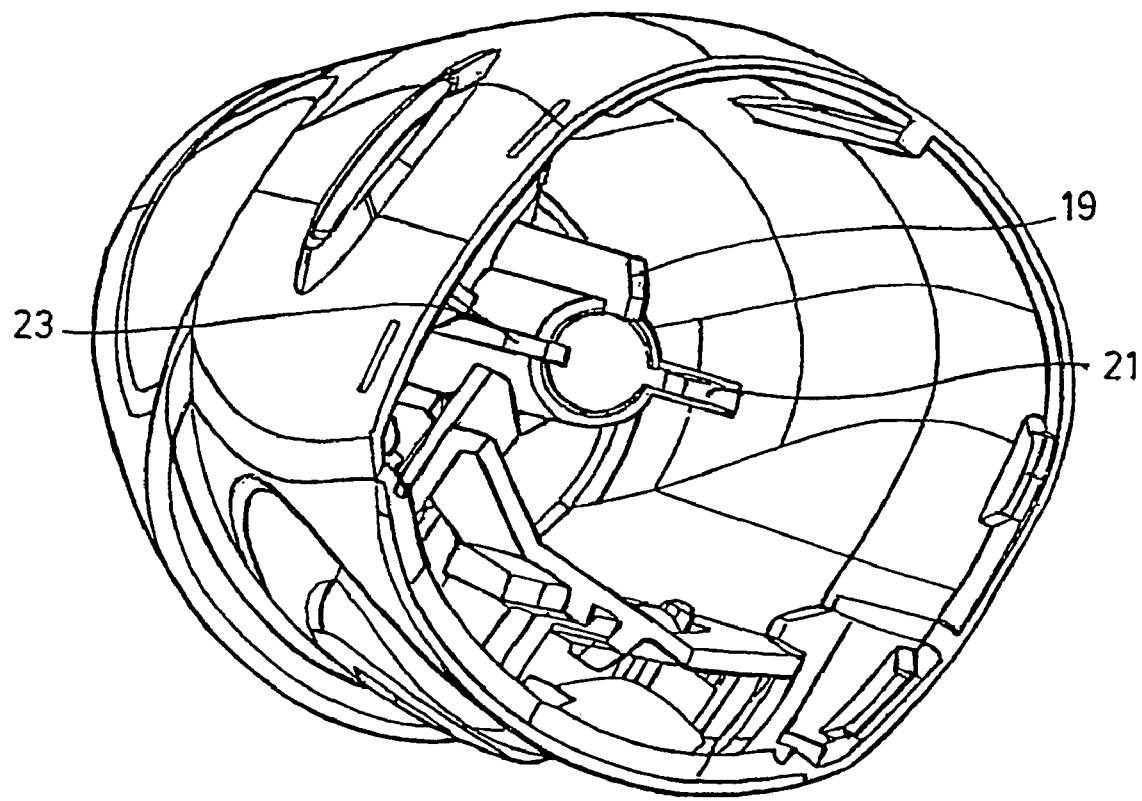
FIG. 16 is a further perspective view of another component of the inhaler.

The shell accommodates an elongate hollow core 10 which is axially and radially fixed at one end to the end (denoted by reference numeral 12) of the shell 2. The core 10 is rotationally and axially fixed to the shell 2. As can be seen from FIG. 15, the bottom of the core 10 is provided with three equi-angularly spaced slots 11, 13 and 15, each defined by a respective pair of opposed ribs which extend towards the core centre. As can be seen from FIG. 16, the end of the shell 2 is provided with three ribs 19, 21 and 23. Each of the ribs 19, 21 and 23 extends a respective one of the slots 11, 13 and 15 in the core 10 (when the inhaler is assembled) and frictionally engaged the ribs defining that slot. The frictional engagement between the ribs on the core 10 and the shell 2 retains the core 10 in and axially and rotationally fixes the core 10 to the shell 2. These formations leave clear an opening 25 in the bottom edge of the core to allow air to travel from an inlet (not shown) up through the core centre.

The core 10 has a bottom portion 18 which is externally screw-threaded and on which a cylindrical dose carrier 20 is mounted. The dose carrier carries a helical array of radial through bores, each of which contains a respective dose of powdered medicament, and is sealed by means of inner and outer laminated foil seals. A more detailed description of this type of container can be found in PCT publication No. WO 95/31238. The present container differs from a container as described in the earlier publication only in that the present container includes indentations (not shown) on its inner cylindrical surface for receiving an end of a locator device 22 as described below.

The container 20 has radial inward protuberances, for example 24, which engage the screw-thread of the bottom portion 18 such that rotation of the container 20 about the axis defined by the core 10 causes the container also to move axially along the core 10 to bring successive compartments into registry with the central portion of an opening 26 (that defines part of an airway in the inhaler) in the core 10. The opening 26 is an axial alignment with the locator 22 which is, in turn, slidably mounted in the core 10 so as to be movable in a direction perpendicular to the core axis. The locator 22 is hollow, has an end opening and slidably contains a pin holder 28 from which a U-section pin 30 extends. The locator 22 has four conical end projections, for example 32 and 34, which, in use, engage corresponding indentations on the inside surface of the container 20. One face of the locator 22 also carries a lug 36 positioned adjacent a generally C-shaped camming aperture 38 in a face of the locator 22.

The pin holder 28 is also provided with a key way 40 which is provided with a forward ramp 42 and is used in the extending and retracting of the pin 30 to rupture the seals on the compartments in the container 20.

Figure 5:
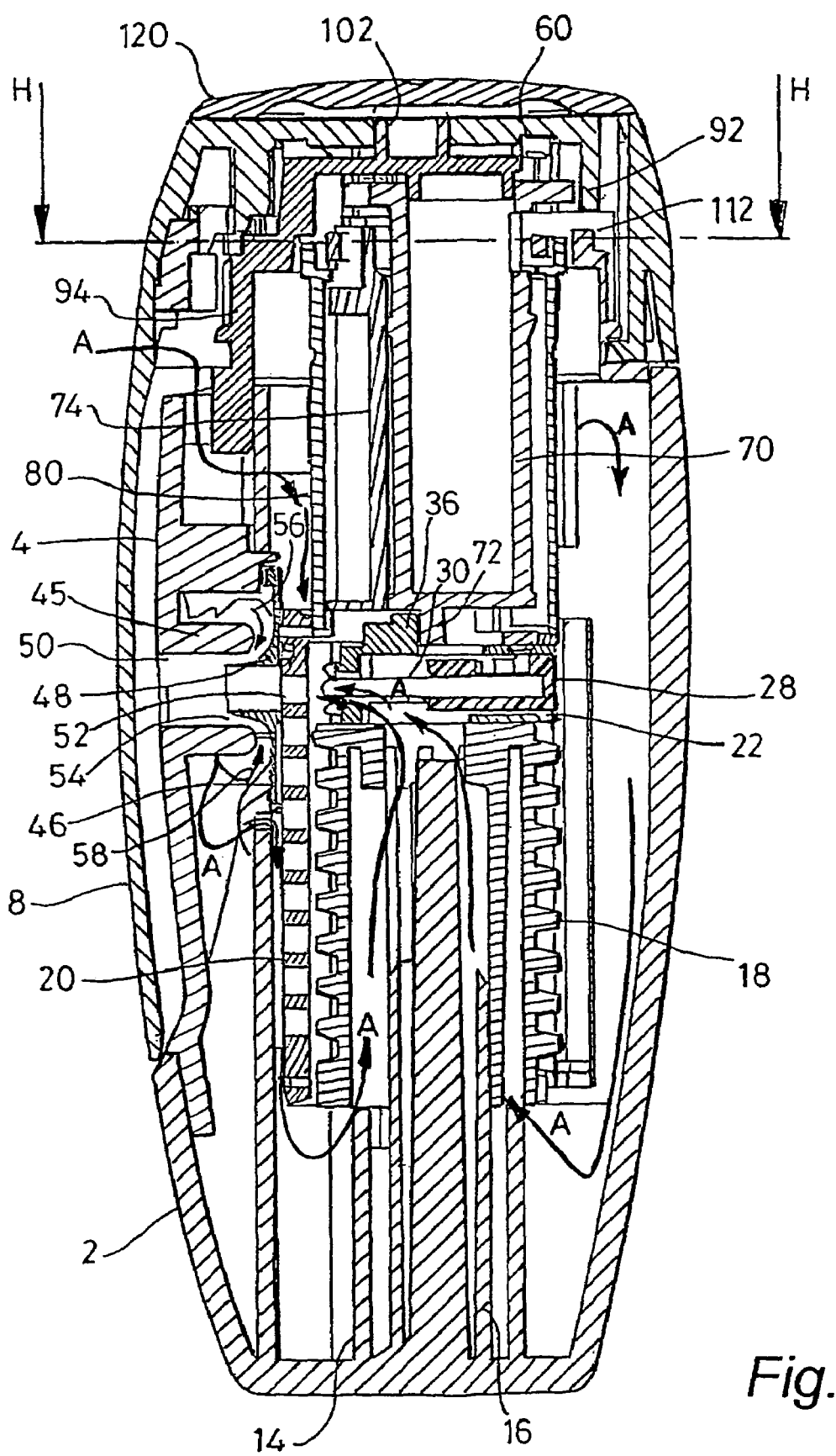
FIG. 5 is a sectional side view of the inhaler.
Figure 6:
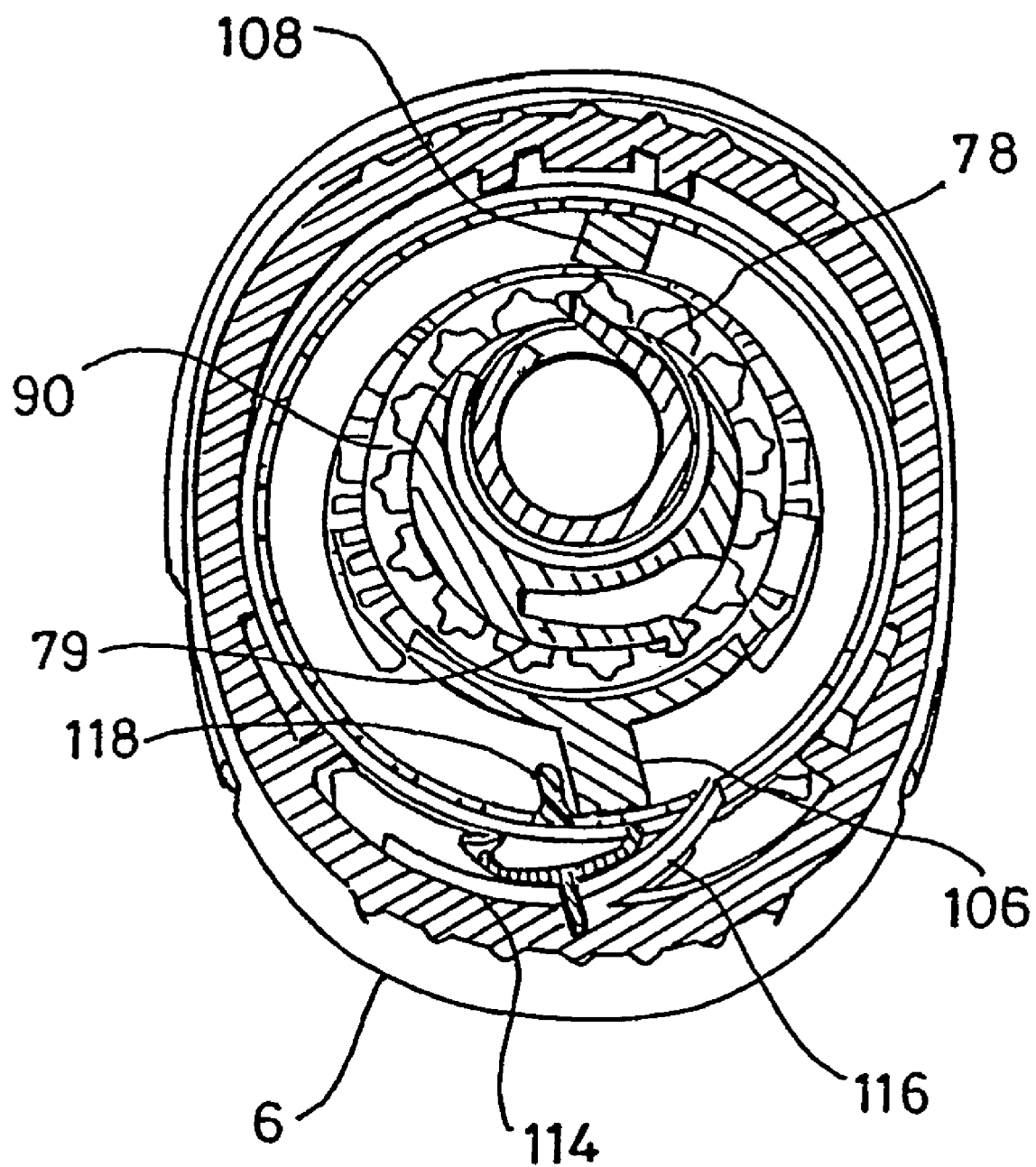
FIG. 6 is a sectional view taken along the line H—H of FIG. 5.
Figure 7:
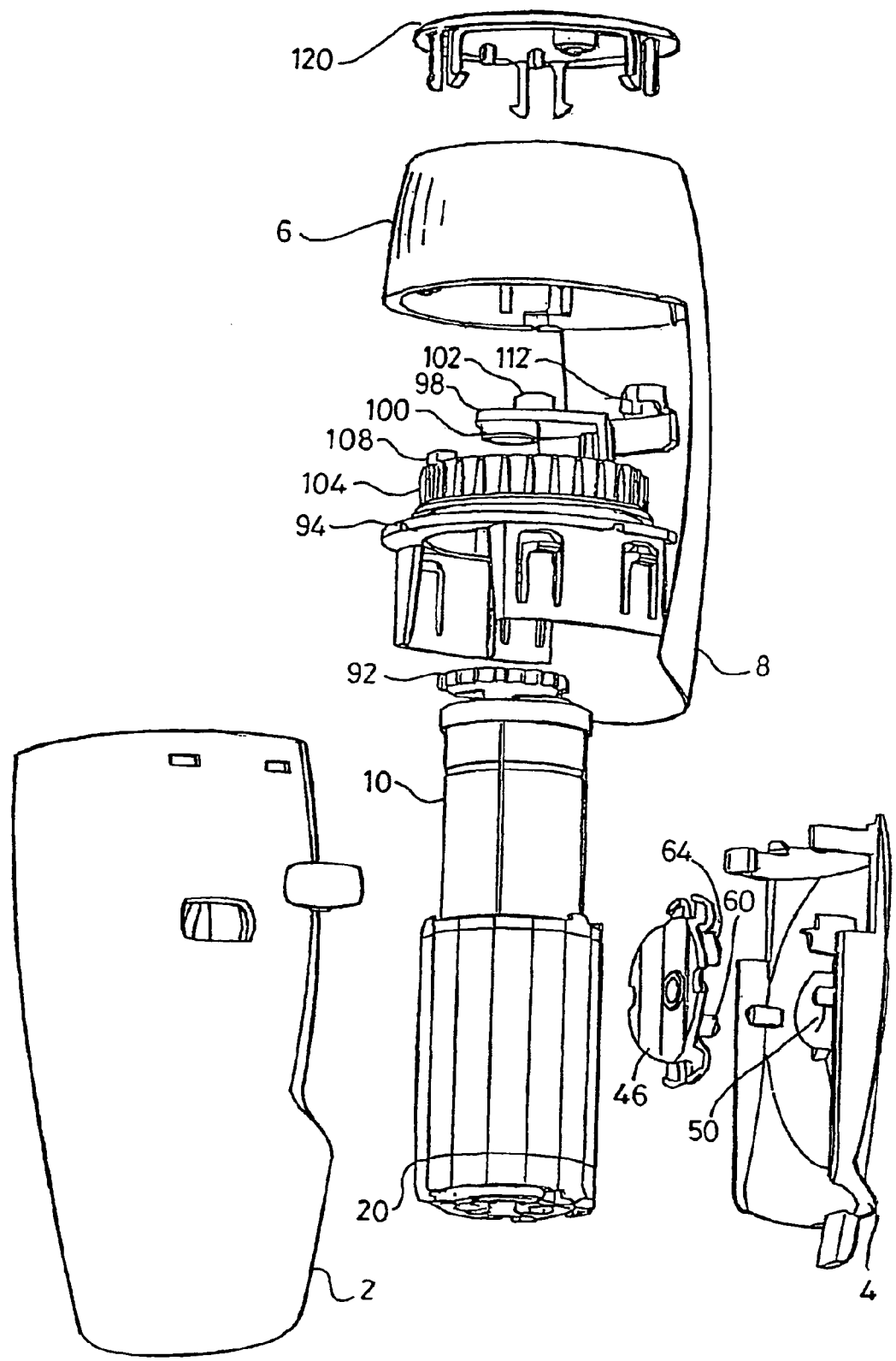
FIG. 7 is a similar view (from a slightly different angle) to FIG. 3.

The pin 30 is axially aligned with a central passage, referenced 44 of an airway insert 46 which fits over a corresponding boss 45 on the mouthpiece 4. As can be seen from FIG. 5, the airway insert 46 has a central passage 48 which extends into a corresponding passage 50 in the boss 45 of the mouthpiece 4, and which is in registry with a compartment (in this case the compartment 52) of the container 20. The portion of the insert 46 defining the passage 48 is spaced from the walls of the passage 50 to define an annular air inlet 54 for air flowing in directions indicated by the arrows 56 and 58. It will be seen from FIG.

5 that the inlet 54 also constitutes a throat as it is narrower than both the upstream portions of the airway that feed it and than the passage 50.

The opening 26 in the core 10 provides the second air inlet which is situated behind a dose in the compartment 52. The insert 46 has four spacer lugs 60, 62, 64 and 66 which are equi-angularly arranged around the passage 50, and which extend generally radially relative to the core 10 and maintain the spacing between the insert 46 and the mouthpiece 4.

The locator 22 is extended by the action of a camming surface 68 (visible in FIG. 2) which bears against the lug 36 and forms part of the end of the drive shaft 70. A peg 72 projects from the same end of the drive shaft 70 and is operable to engage the slot 38 to retract the locator 22. The peg also engages the key way 40 in the holder 28 to extend and retract the pin 30.

The core 10 has an upper portion 74 into which the drive shaft 70 is inserted. As can be seen from FIG. 2, one side of the upper portion 74 includes a slot 76 which allows a pawl 78 on the drive shaft 70 to extend radially beyond the upper portion 74 when the pawl is in registry with the slot 76.

Figure 3:
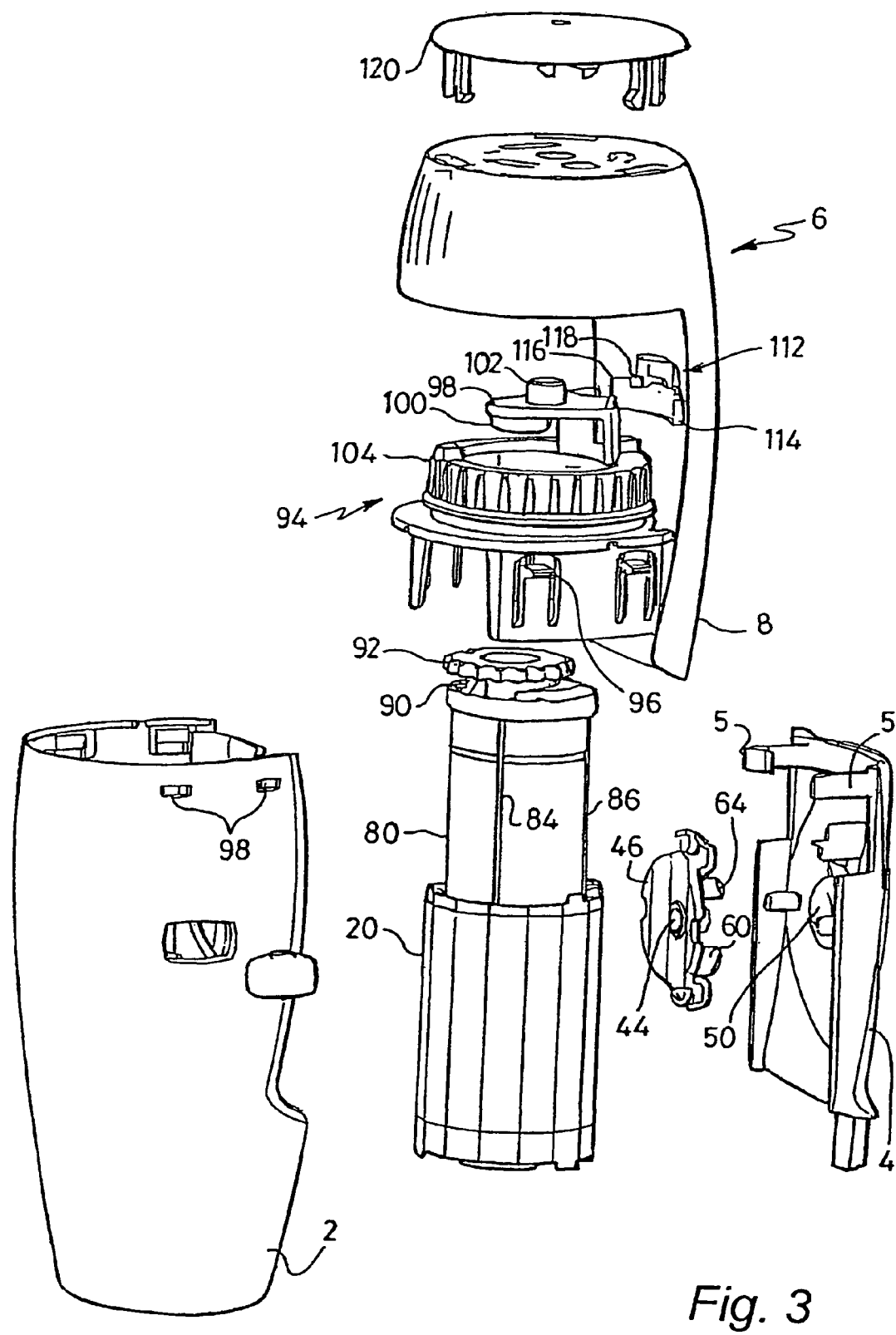
FIG. 3 is a further exploded view of the inhaler, showing certain components in an assembled form.
Figure 4:
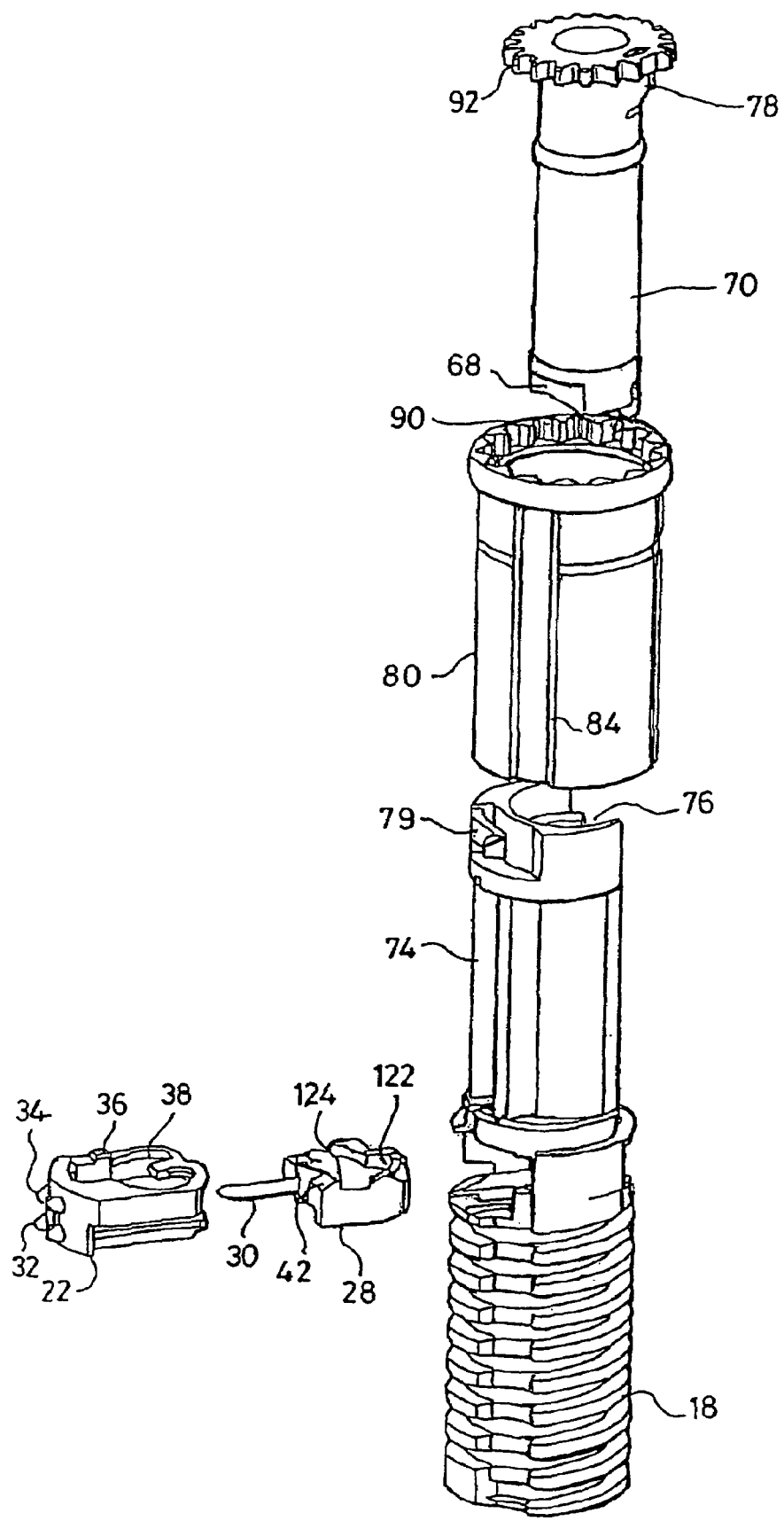
FIG. 4 is an exploded view of those components.

As can be seen from FIG. 3, the upper portion 74 and shaft 70 both fit within a generally cylindrical index collar 80. The collar 80 is fitted onto the upper portion 74 before the shaft 70 is inserted, and is rotatably retained on the upper portion, and axially located by the annular shoulder 82 defined by the top of the lower portion 18 of the core 70.

A further pawl 79 is situated on the outside of the upper portion 74 at a position generally opposite the slot 76.

The index collar 80 has a series of longitudinal external slots, for example, 84 and 86 which engage corresponding inwardly directed lugs, for example 88, on the container 20. The relative dimensions of the container 20 and index collar 80 are such that the container 20 can slide along the outside of the index collar 80, but is rotationally fixed to the collar by the engagement of fixed lugs in the slots in the collar. Thus, rotation of the index collar 80 will cause a corresponding rotation of the container 20 which therefore also travels axially along the core 10 as a result of its engagement with the screw-threaded portion 18.

A ring gear 90 is provided at the end of the collar 80 opposite the end which rests on the shoulder 82. The teeth of the gears 90 are inwardly directed, and are, in use, engaged by the pawls 78 and 79. In the described embodiment, the shapes of the ends of the pawls and of the teeth are such that the pawls can be pulled over one tooth onto the next, but cannot readily be pushed in the opposite direction.

A gear wheel 92 is provided at the end of the drive shaft 70 in such a position as to protrude from the end of the sub-assembly of the core 10, container 20, indexing collar 80 and drive shaft 70.

Figure 17:
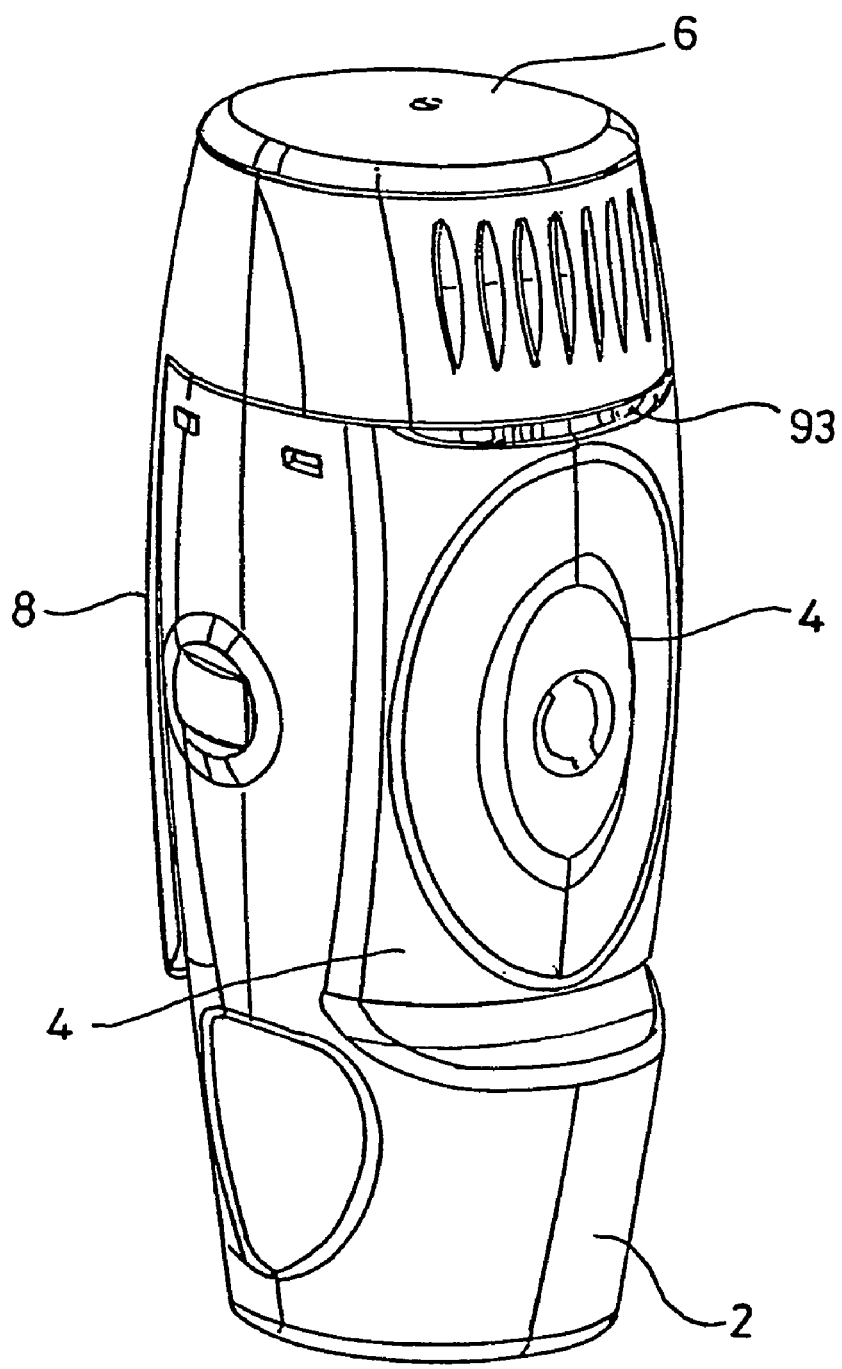
FIG. 17 is a perspective view of the inhaler, when assembled and with its mouthpiece uncovered.

The mouthpiece 4 has latching components, for example 5, which engage in corresponding recesses/apertures in the shell 2 so that the mouthpiece 4 can be snap-fitted into position on the shell 2. With reference to FIG. 17, an end of the mouthpiece 4 is spaced from the shell 2 and control member 6 to define an air inlet 93. When a user inhales through the mouthpiece 4, air travels through the inhaler from the inlet 94 to the mouthpiece 4 generally along the path indicated by the arrows A in FIG. 5. As can be seen, air flows towards and through the opening 25, up the hollow interior of the core 10, and through the pin 30, locator 22 and dose cavity 52.

The sub-assembly is radially located by means of an inner cap 94 which has latching components 96 for engaging corresponding apertures 98 in the shell 2 to retain the cap 94 in position thereon. The cap 94 has an end stop 98 which carries a boss which is in axial alignment with the circular aperture 93 in the gear wheel 92. The end stop 98 also carries a second boss 102 the axis of which is spaced from that of the boss 100, and which extends in the opposite direction from the other boss. The inner cap 94 also incorporates an annular component 104, the outer surface of which carries a number of gear teeth. The component 104 also carries a pair of stops 106 and 108 which project axially from the end face of the component 104.

The member 6 is rotatably mounted on the boss 102 and incorporates a ring 110 (FIG. 2) of inwardly directed teeth for meshing with the teeth on the gear wheel 92 of the shaft 70. A carrier device 112 is also mounted on the inside of the member 6, and carries a pair of oppositely directed pawls 114 and 116. The carrier 112 has an actuator 118 which projects radially inwards and (in use) engages either of the stops 106 or 108 (depending on the position of the member 6) to rock the carrier 12 so as to bring one or other of the pawls 114 and 116 into engagement with the teeth on the annular component 104. An end piece 120 clips onto the member 6 to conceal tooling holes in the end of the latter.

The member 6 is rotatable through approximately 180°, and one cycle of movement of the member comprises rotation in one direction about 180° and then rotation in the reverse direction through the same angle to return the member to its original position. This motion pierces the foil seal of a compartment 20 in registry with the pin 30 (and hence the airway defined by the insert 46 and mouthpiece 4), whilst uncovering the exit of the passage 50 to enable the user to inhale a dose through that exit, and then indexes the container 20 so that the next full compartment is in registry with the airway, and covers the mouthpiece. This cycle of operation will be described in more detail with reference to FIGS. 8–14.

FIGS. (8–14)A illustrate the effect of the rotation of the cover member 6 on the locator 22, FIGS. (8–14)B the effect of the same rotation on the pin holder 28 (and hence the pin 30), FIGS. (8–14)C the effect on the indexing mechanism, constituted by the indexing collar, the upper portion of the core 74 and the shaft 70, and FIGS. (8–14)D the effect on the non-return mechanism provided by the component 112 by the teeth 94 and the stops 106 and 108.

With the device in a start position shown in FIGS. 8A–D, the sealed, full compartment of the container 20 is in registry with the pin 30 and the airway defined by the passages 48 and 50. Thus, in order to make the contained dose available for inhalation, it is necessary to pierce the two sheets of foil which seal that compartment.

Figure 9A:
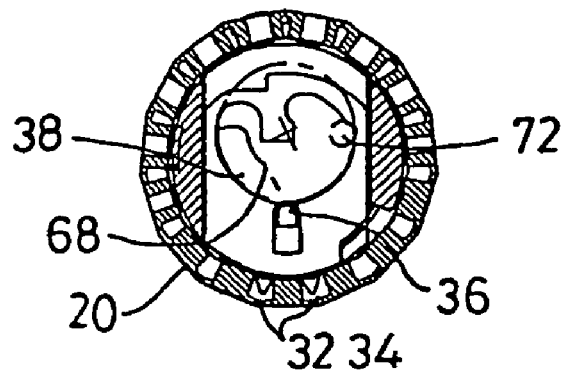
Figure 9B:
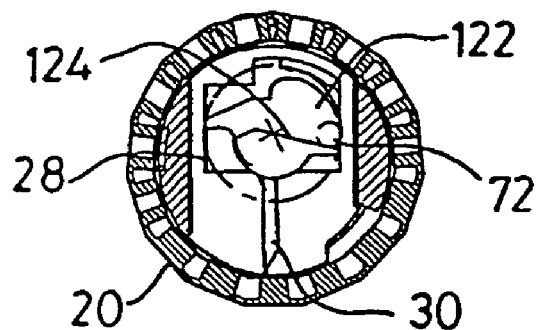
Figure 9C:
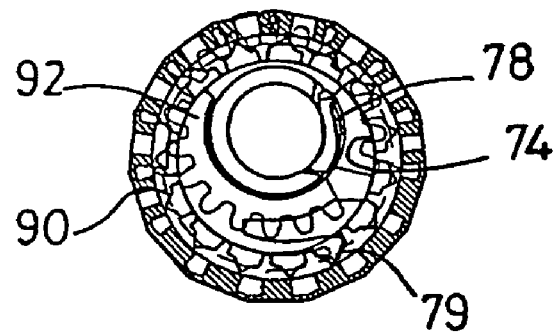
Figure 9D:
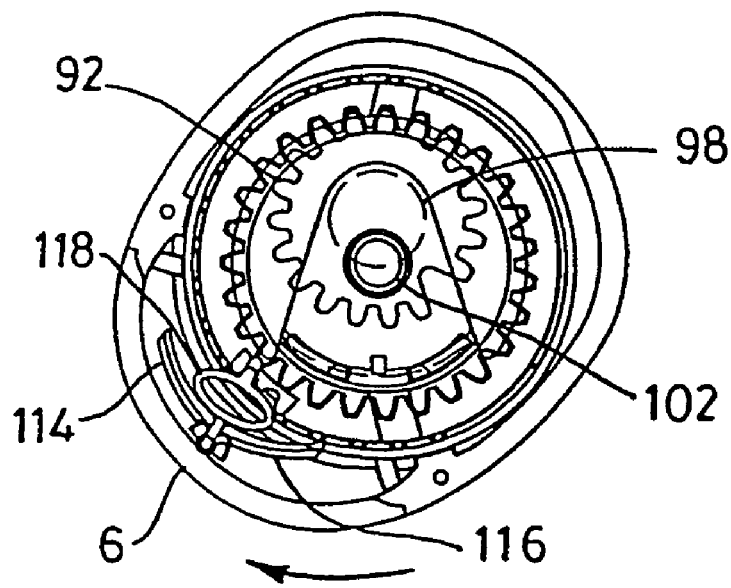

To that end, the cap 6 is rotated relative to the shell 2 in a clockwise direction as indicated in FIG. 9D. This causes the ring of gear teeth 110 to rotate the gear wheel 92 and hence the shaft 70 in the same clockwise direction. The rotation of the shaft 70 brings the camming surface 68 on the base of that shaft into engagement with the lug 36 on the locator 22, causing the locator to extend into the position shown in FIG. 9A, in which the cones (for example 32 and 34) on the end of the locator 22 extend into corresponding recesses in the container 20, firmly to locate the compartment relative to the pin 30. During this phase of movement, the peg 72 passes along a circumferential portion (122 in FIGS. 8B and 9B), which corresponds to the arc of movement of the peg 72. As a result, the pin 30 remains retracted within the core 10 during this first phase of operation of the device.

Figure 8A:
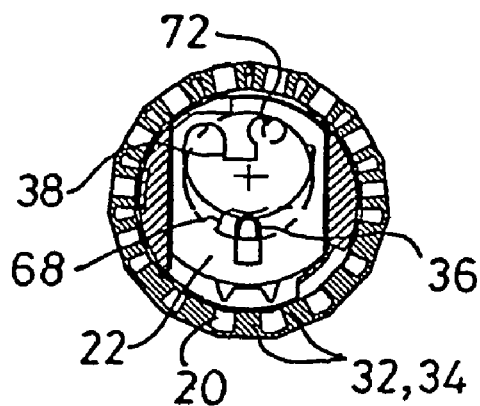
FIGS. 8A–D to FIGS. 14A–D are cut-away end views of the inhaler during various stages in one cycle of its operation.
Figure 8B:
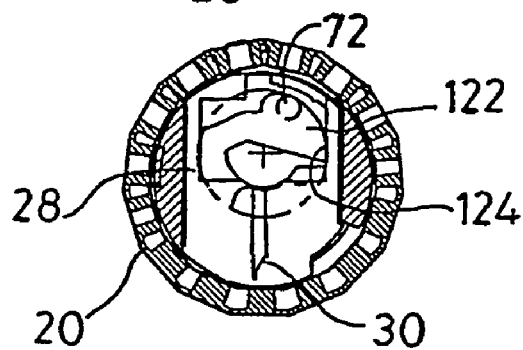
Figure 8C:
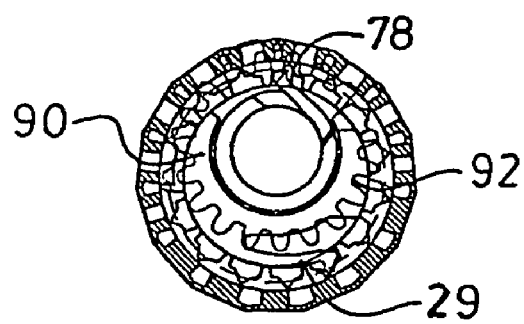
Figure 8D:
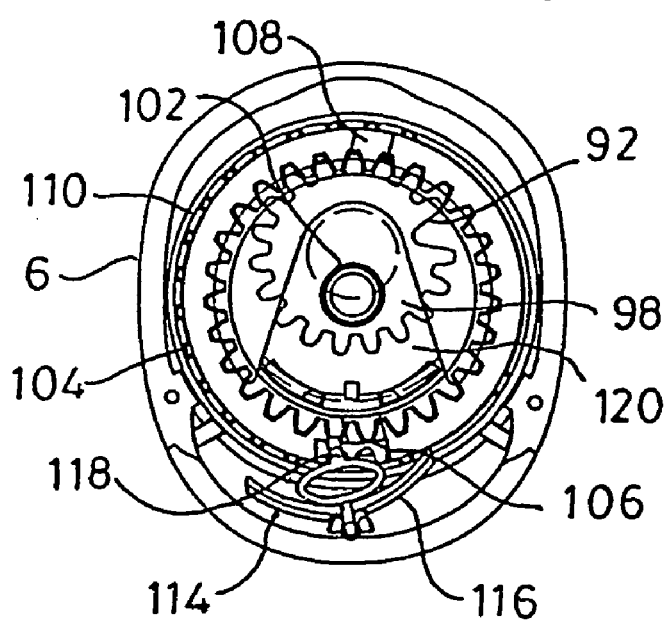
Figure 10A:
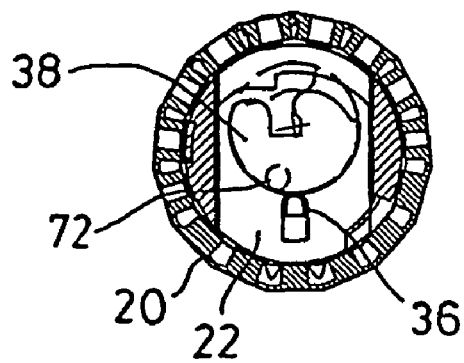
Figure 10B:
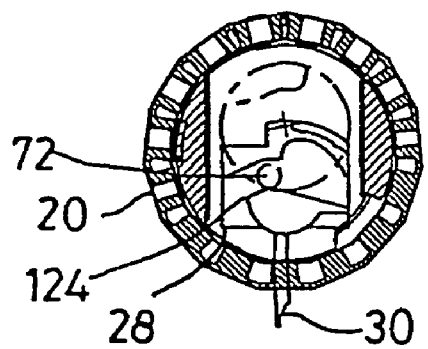
Figure 10C:
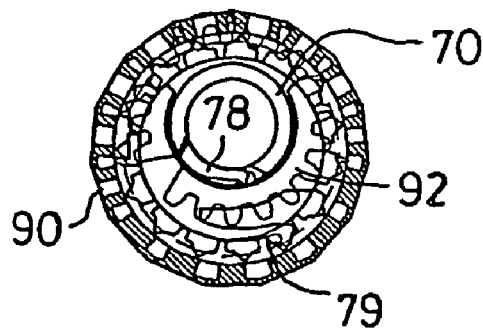
Figure 10D:
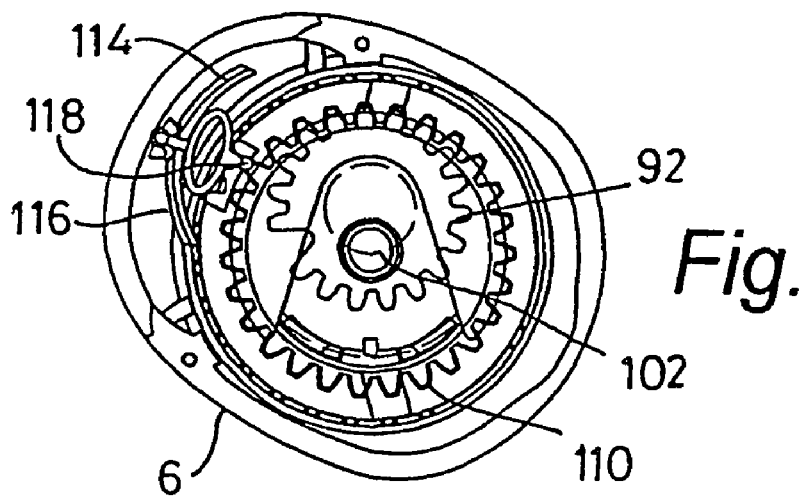

FIG. 9B shows the peg when it has reached a non-circumferential portion 124 of the key way 40. Consequently, further rotation of the cover 8 in the same direction will then extend the pin 30 as shown in FIG. 10B. This movement of the pin 30 causes it to travel through the compartment, and thus to pierce both foil seals on either side of the compartment. The sectional shape of the pin 30 is such that this movement does not eject any significant amount of the material to be inhaled from the compartment. The initial rotation of the control member 6 causes the pawl 78 on the shaft 70 to be withdrawn into the upper portion 74 of the core 10 so that it cannot engage the teeth 90 on the indexing collar 80. It can also be seen from FIGS. 8D, 9D and 10D that the pawl 116 engages the ring of teeth 110 on the inner cap 94. The pawl 116 thus allows the rotation of the control member 6 in an anti-clockwise direction, but prevents rotation in the opposite sense. The continuing anti-clockwise rotation of the control member 6 into the position shown in FIG. 11D causes the peg 72 to engage a further surface 126 of the key way 40, and thus to withdraw the pin 30 from the compartment. Again, the shape of the pin 30 is such that its withdrawal does not remove any substantial amount of particulate material from the compartment. During this movement of the cover member 6, the camming surface 68 continues to hold the locator 22 in engagement with the container 20, and the upper portion 76 of the core 10 continues to keep the pawl 78 out of engagement with the teeth 90 of the indexing collar 80. As the cover 8 has been rotated to the opposite side of the shell 2 from the mouthpiece 4, the exit 50 is at this stage accessible to a user who can inhale the dose of material from the compartment. Inhalation by the user through the mouthpiece 4 creates a stream of air flowing into the passage 50 through the annular inlet 54. The airway insert and passage 50 define between them a throat which accelerates this flow of air, thus creating an area of low pressure in front of the passage 48, and hence the dose in the compartment 52, and this helps to establish a stream of air flowing through the compartment 52 and into the passage 50, in which stream of air the dose is entrained. As the dose leaves the ejection zone, (defined in this case by the compartment 52 and passage 48) the air flowing in through the inlet 54 forms a jacket which prevents the entrained dose from significantly impinging on the walls of the passage 50.

Figure 11A:
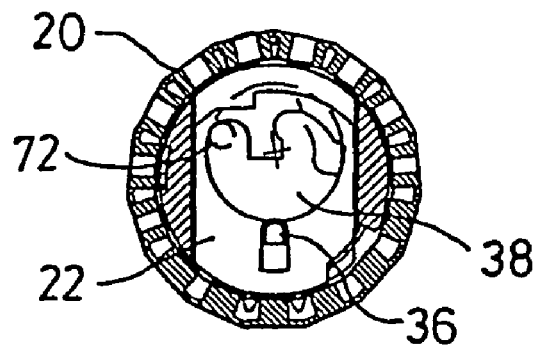
Figure 11B:
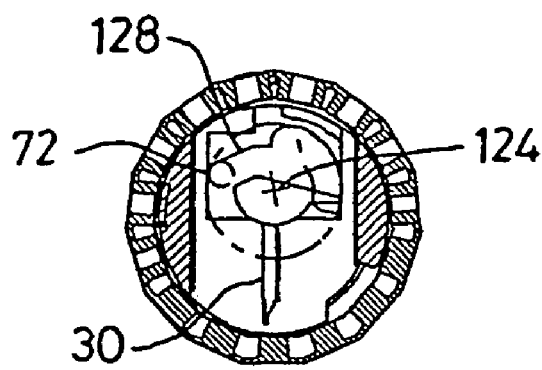
Figure 11C:
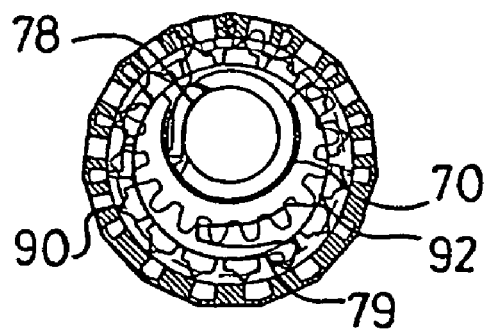
Figure 11D:
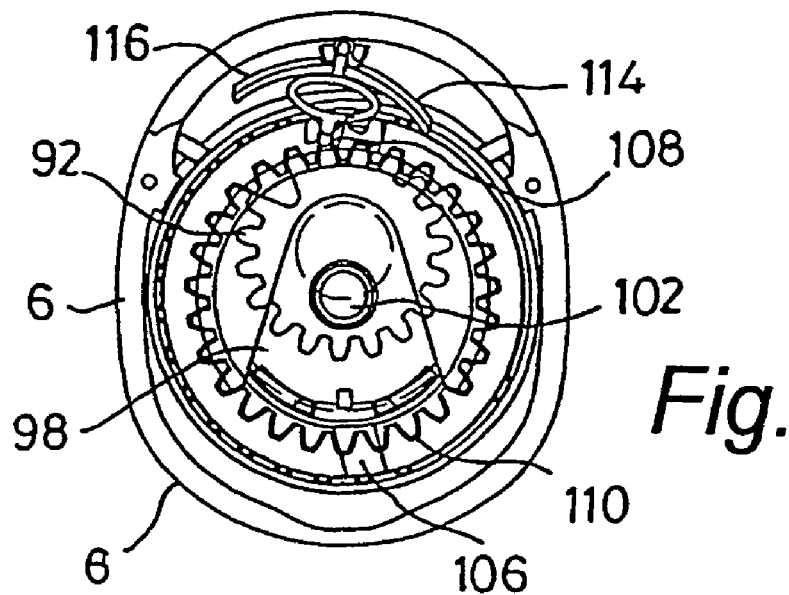
Figure 12A:
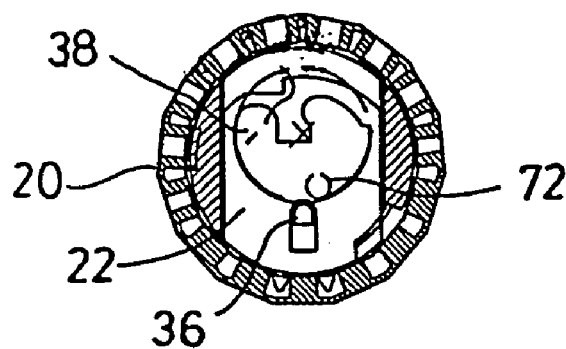
Figure 12B:
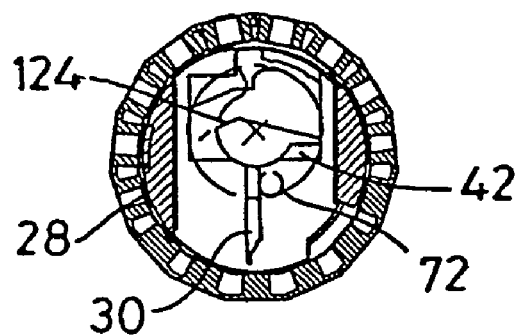
Figure 12C:
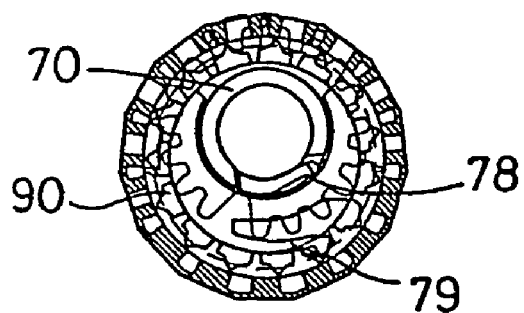
Figure 12D:
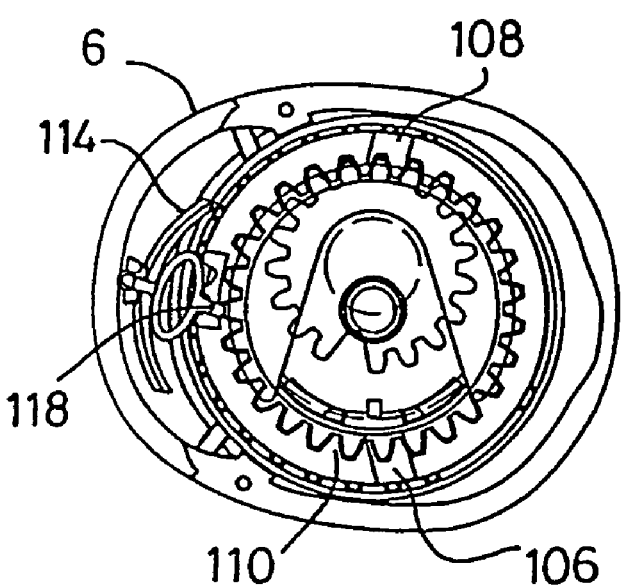

As can be seen from FIG. 11D, the actuator 118 of the carrier 112 has been rocked by the stop 108 so as to bring the pawl 114 into engagement with the teeth and to disengage the pawl 116. Since the pawl 116 is now disengaged, the control member can be rotated in the opposite sense (i.e. clockwise), but the pawl 114 will prevent anti-clockwise rotation until the control member 6 has been returned to its start position.

Figure 13A:
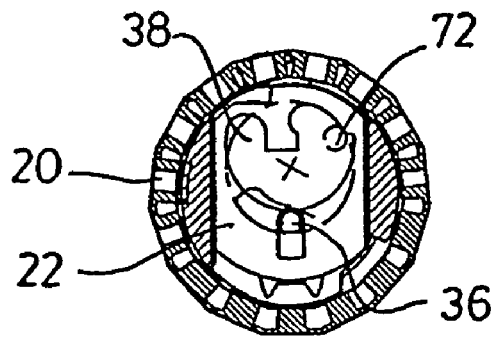
Figure 13B:
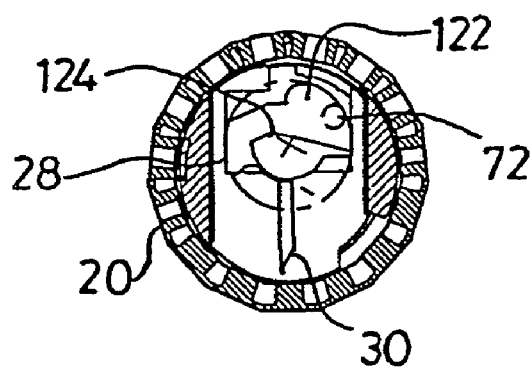
Figure 13C:
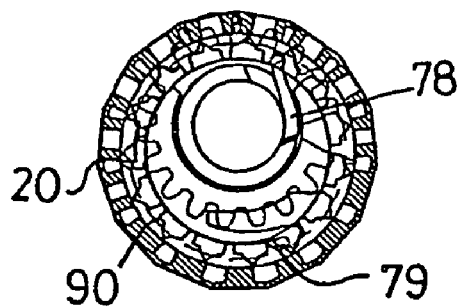
Figure 13D:
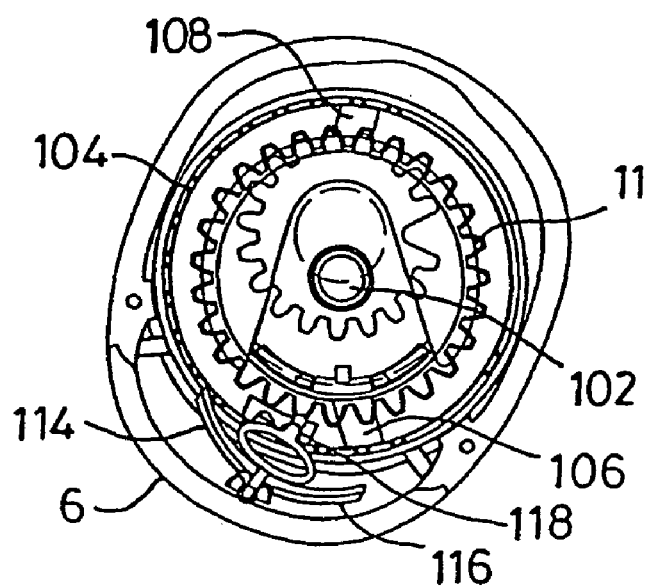
Figure 14A:
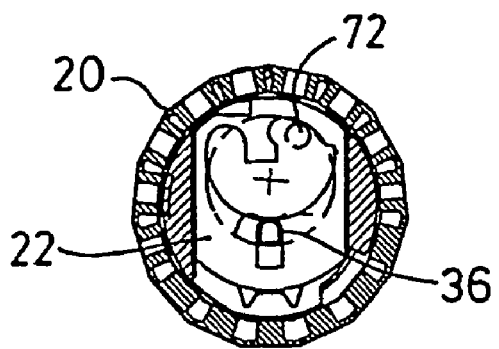
Figure 14B:
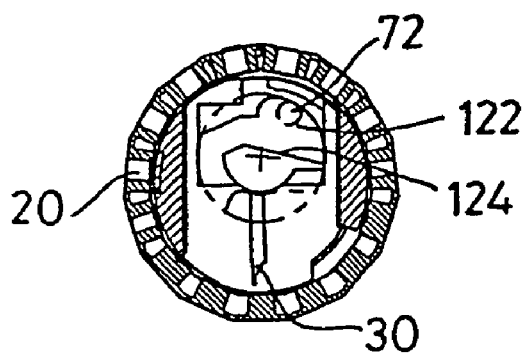
Figure 14C:
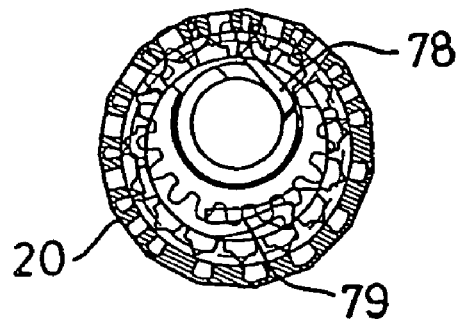
Figure 14D:
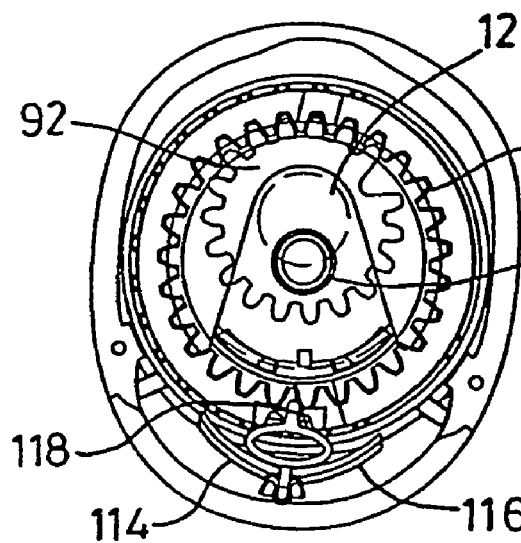

With reference to FIGS. 12A–D, as the control member 6 returns to its start position, the shaft 70 rotates within the core 10 to move the pawl 78 towards the slot 76. In addition, the peg 72 passes in front of the pin holder 28 and towards the inclined ramp 42. Continued clockwise rotation of the control member 6 moves the camming surface 68 out of engagement with the lug 36 and the peg 72 into engagement with the camming aperture 38, and thus causes the locator 22 to be withdrawn back into the core 10. The movement also causes the pawl 78 to extend out of the slot 76 and into engagement with one of the teeth 90 in the indexing collar 80 (FIG. 13C). Continued rotation of the control member 6 then causes the pawl 76 to push the indexing collar 80 in an anti-clockwise direction as viewed from FIG. 13C, thus allowing the pawl 79 to ride over a tooth of the gear 90. This rotation of the indexing collar 80 correspondingly rotates the container 20, and moves the container in a small axial direction towards the inner cap 94 by virtue of the screw-threaded engagement with the portion 18. Thus, the container 20 is indexed into the next position in which the next compartment is in registry with the pin 30 and the airway 48. FIG. 14D shows the cover member when it is close to its original position, at which stage the actuator 118 engages the stop 106 to move the carrier 112 back to its original position (in which it is the pawl 116 that engages the teeth 94). It will be appreciated that the pawl 79 stops the collar 80 (and hence the container 20) rotating as the control member is moved in a clockwise direction, whilst allowing movement of the member in the other direction to index the container 20.

In addition, since the gear wheel 92 is of a smaller diameter than the ring of teeth 110, a rotation of 180° of the control member 6 causes the shaft 70 to rotate through a larger angle, thus enabling the peg 76 both to extend and withdraw the pin 30 in response to the rotation of the cover member from the start position to the position shown in FIG. 11D.

In this particular example, that movement of the cover member constitutes an advanced stroke, whilst the return, anti-clockwise movement position shown in FIG. 8D is a return stroke of the cover member 6.

Figure 18:
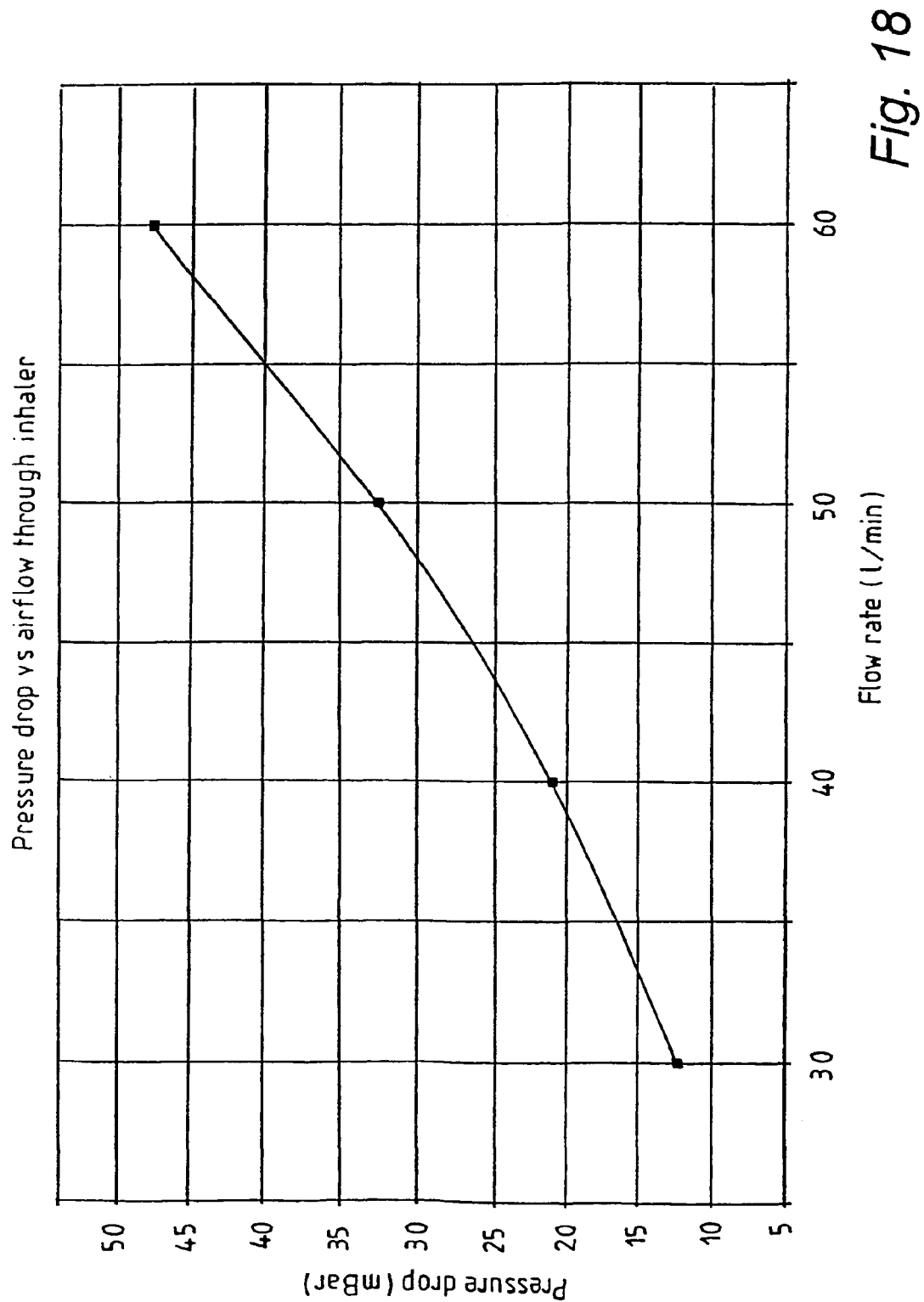
FIG. 18 is a graph illustrating the relationship between pressure drop in the inhaler and the rate of airflow therethrough.

FIG. 18 is a graph illustrating the relationship between the pressure drop along the passage 48 and the total rate of flow of air through the inhaler. The graph shows that even low flow rates provide a significant pressure drop. The inhaler design thus helps to ensure that a full dose of powder is inhaled even if the user is unable to inhale properly.

What is claimed is:

1. A device for dispensing doses of particulate material, the device comprising an airway having a wall, an inlet means and an outlet through which the doses are dispensed, a receiver for receiving and retaining a dose of material in an ejection zone in registry with the airway, from which ejection zone, in use, a dose travels though the airway to the outlet, wherein the inlet means includes at least one inlet which surrounds the ejections zone, and hence a dose therein, and is so positioned as to direct a flow of air into the airway at a region between a dose exiting the ejection zone and the wall of the airway, thereby providing, in use, a jacket of air, flowing from the ejection zone to the exit, which prevents particles of the ejected dose from impinging on the airway walls, the inlet means also including a further inlet situated behind the ejection zone so that the latter is interposed between the further inlet and the outlet, wherein, in use, the pressure of air passing through the further inlet ejects the dose from the ejection zone.

2. A device according to claim 1 in which the inlet means comprises an annular inlet.

3. A device according to claim 1, in which the inlet means is so configured as to accelerate the flow of the air which is to define said jacket of air as that air enters the airway, thereby to create a zone of low pressure in front of the ejection zone.

4. A device according to claim 1, in which the receiver is so arranged as to receive a container having a plurality of compartments, each containing a respective dose, and the device includes indexing mechanism for moving the container so as to bring successive compartments into the ejection zone.

5. A device according to claim 4, in which the receiver comprises an elongate cylindrical cavity for receiving a cylindrical container having a plurality of radial apertures, each constituting a respective compartment, the device an having indexing mechanism for rotating the container about and moving the container along, its axis so as to bring successive apertures into said ejection zone.

6. A device according to claim 4, in which the airway has a portion which extends from the ejection zone to a mouthpiece and which is substantially radial relative to said cylindrical cavity.

7. A device according to claim 4, in which the device is arranged for use with a container having at least one pierceable seal for individually encapsulating the doses, the device including a piercing mechanism for piercing the seal to allow each dose, in turn, to be dispensed, wherein the piercing mechanism and indexing mechanism are operatively linked to a control member movable in one direction to operate the indexing mechanism and in the other to operate the piercing mechanism, the device including a non-return mechanism for preventing movement of the control member in one of the directions until the previous stroke of movement in the other direction has been completed.

8. A device according to claim 7, in which the control member is rotatable, and the non-return mechanism comprises a two-way ratchet mechanism operable to ensure that, for both senses of rotational movement of the member, a full stroke of movement in each sense is completed before the next stroke of movement in the opposite sense commences.

9. A device according to claim 8, in which the non-return mechanism comprises a pair of oppositely directed pawls on a carrier mounted on the control member era body of the device, and operable to engage teeth fixed relative to the other of the control member and the body of the device, the mechanism further comprising at least one abutment for engaging the carrier at the end of each stroke to move one pawl out of engagement with the teeth and bring the other pawl into said engagement.

10. A device according to claim 1, in which the device constitutes an inhaler for dispensing doses of a powered medicament by inhalation, the inhaler having a mouthpiece, and the outlet of the airway forming part of the mouthpiece.

* * * * *